United States Patent
Maloney et al.

(10) Patent No.: US 10,512,596 B2
(45) Date of Patent: Dec. 24, 2019

(54) ORAL COMPOSITION FOR TOOTH WHITENING

(71) Applicant: Colgate-Palmolive Company, New York, NY (US)

(72) Inventors: Venda Maloney, Piscataway, NJ (US); Suman Chopra, Monroe, NJ (US); Hallena Strotman, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/533,466

(22) PCT Filed: Dec. 19, 2014

(86) PCT No.: PCT/US2014/071441
§ 371 (c)(1),
(2) Date: Jun. 6, 2017

(87) PCT Pub. No.: WO2016/099544
PCT Pub. Date: Jun. 23, 2016

(65) Prior Publication Data
US 2017/0326039 A1  Nov. 16, 2017

(51) Int. Cl.
| | |
|---|---|
| *A61K 8/02* | (2006.01) |
| *A61Q 11/00* | (2006.01) |
| *A61K 8/73* | (2006.01) |
| *A61K 8/21* | (2006.01) |
| *A61K 8/34* | (2006.01) |
| *A61K 8/44* | (2006.01) |
| *A61K 8/81* | (2006.01) |

(52) U.S. Cl.
CPC .............. *A61K 8/0254* (2013.01); *A61K 8/21* (2013.01); *A61K 8/345* (2013.01); *A61K 8/44* (2013.01); *A61K 8/731* (2013.01); *A61K 8/8164* (2013.01); *A61Q 11/00* (2013.01); *A61K 2800/28* (2013.01); *A61K 2800/43* (2013.01); *A61K 2800/5422* (2013.01); *A61K 2800/5424* (2013.01)

(58) Field of Classification Search
CPC .................................................. A61K 8/0254
See application file for complete search history.

(56) References Cited

U.S. PATENT DOCUMENTS

| | | | |
|---|---|---|---|
| 4,376,763 A | 3/1983 | Barth et al. | |
| 4,443,564 A | 4/1984 | Hauischild et al. | |
| 4,444,746 A | 4/1984 | Harvey et al. | |
| 6,030,222 A | 2/2000 | Tarver | |
| 6,669,929 B1 | 12/2003 | Boyd et al. | |
| 7,763,235 B2 | 7/2010 | Boyd et al. | |
| 8,147,814 B2 | 4/2012 | Song et al. | |
| 8,475,771 B2 | 7/2013 | Boyd et al. | |
| 9,498,410 B2 | 11/2016 | Boff et al. | |
| 9,510,668 B2 | 12/2016 | Patel et al. | |
| 9,522,111 B2 | 12/2016 | Szewczyk et al. | |
| 9,675,540 B2 | 6/2017 | Gu et al. | |
| 9,744,112 B2 | 8/2017 | Szewczyk et al. | |
| 9,750,825 B2 | 9/2017 | Szewczyk et al. | |
| 9,827,172 B2 | 11/2017 | Xu et al. | |
| 9,918,909 B2 | 3/2018 | Boyd et al. | |
| 2004/0136924 A1 | 7/2004 | Boyd et al. | |
| 2005/0019273 A1 | 1/2005 | Boyd et al. | |
| 2012/0082628 A1 | 4/2012 | Haight et al. | |
| 2012/0093905 A1 | 4/2012 | Batchelor et al. | |
| 2012/0270183 A1 | 10/2012 | Patel et al. | |
| 2013/0095159 A1* | 4/2013 | Boyd ...................... A61K 8/02  424/401 |
| 2015/0086486 A1 | 3/2015 | Szewczvk et al. | |
| 2016/0331663 A1 | 11/2016 | Maloney et al. | |
| 2017/0027824 A1 | 2/2017 | Maloney et al. | |
| 2017/0042317 A1 | 2/2017 | Patel et al. | |

FOREIGN PATENT DOCUMENTS

| | | |
|---|---|---|
| CN | 102725026 | 10/2012 |
| CN | 103491825 | 1/2014 |
| EP | 1935395 | 6/2008 |
| EP | 2087903 | 8/2009 |
| EP | 2197998 | 12/2012 |
| RU | 2307644 | 10/2007 |
| WO | WO 2003/035771 | 5/2003 |

(Continued)

OTHER PUBLICATIONS

Author Unknown, "What's in toothpaste'MNN—Mother:"Mature Network, Nov. 3, 2014, http://www.mnn.com/health/fitness-well-being/stories/whats-in-toothpaste, accessed Nov. 3, 2014, pp. 1-15.
Author Unknown, 2014, Luster Premium White Toothpaste, http://www.lusterpremiumwhite.com/shop-now-3pack-toothpaste/, accessed Nov. 6, 2014, pp. 1-4.
Colgate-Palmolive, 2014, "Anti-Cavities Fluoride Instant Toothpaste," Database Mintel GNPD AN: 2815171.
Colgate-Palmolive, 2014, "Instant Whitening Effect Fluoride Toothpaste," Database Mintel GNPD AN: 2652789.

(Continued)

*Primary Examiner* — Benjamin J Packard

(57) ABSTRACT

A tooth whitening oral care composition is made by combining ingredients comprising flakes of a water soluble whitening film, a dye with a hue angle in the CIELAB system ranging from 200 to 320 degrees, and an orally acceptable carrier vehicle. The flakes of the water soluble whitening film comprise: (a) a film-forming polymer comprising hydroxyalkyl cellulose wherein the hydroxyalkyl cellulose has a viscosity of about 1 to about 1000 millipascal seconds (mPa·s) as determined as a 2% by weight aqueous solution of the film-forming polymer at 20 C using a Ubbelohde tube viscometer; and (b) a pigment with a hue angle in the CIELAB system ranging from 200 to 320 degrees.

17 Claims, No Drawings

(56) References Cited

FOREIGN PATENT DOCUMENTS

| WO | WO 2007/016394 | 2/2007 |
|---|---|---|
| WO | WO 2009/071451 | 6/2009 |
| WO | WO 2013/047826 | 4/2013 |
| WO | 2013/089759 | 6/2013 |
| WO | 2013/089760 | 6/2013 |
| WO | WO 2013/089761 | 6/2013 |
| WO | WO 2014/117904 | 8/2014 |
| WO | 2015/099640 | 7/2015 |
| WO | WO 2015/099638 | 7/2015 |
| WO | WO 2015/099642 | 7/2015 |

OTHER PUBLICATIONS

International Search Report and Written Opinion of the International Searching Authority in International Application No. PCT/US2014/071441, dated Jul. 10, 2015.

Tian et al., 2011, "Chapter 11: Facial Expression Analysis," Handbook of Face Recognition, Jan. 1, 2015, Springer, New York, US. URL: https://www.cs.cmu.edu/~cga/behavior/FEA-Bookchapter.pdf.

\* cited by examiner

ORAL COMPOSITION FOR TOOTH WHITENING

BACKGROUND

The present disclosure is directed to an oral care composition for whitening teeth.

Many individuals are dissatisfied with their current tooth color. Thus, there is a desire for whiter teeth which can be achieved through the use of tooth whitening products. The whitening effect can be produced by chemically altering or removing the stain and/or changing the visual perception of the color of the teeth.

It is known in the literature that the visual perception of a white substance can be altered through the deposition of an optical brightener, blue pigment or blue dye, especially one for which the hue angle (in the CIELAB scale) of the reflected or emitted light is between 200 to 320 degrees. This effect is commonly used in laundry detergent products to make white clothes appear "whiter" to the human eye.

The same concept has been applied to tooth whitening. The natural off-white or yellow color of teeth can be made to appear whiter through the deposition of a blue substance onto teeth. Using pigments with a deposition aid, such as Gantrez® (copolymers of maleic anhydride and with methyl vinylether) or hydroxypropylmethyl cellulose, in toothpaste to make teeth look whiter is disclosed in EP1935395B1.

Dyes are also known in the art for whitening teeth. For example, U.S. Pat. No. 6,030,222 discloses depositing dyes on teeth for whitening when blended with a carrier. US Patent Application Publication 2012/0093905 discloses dyes coupled to certain polymers for whitening teeth. However, dyes have significantly different properties than pigments. In particular, dyes are much more soluble in water than pigments. The solubility of dyes makes them more difficult to deposit and be retained on teeth in a hydrated environment, as described for example, in EP1935395B1.

Additional tooth whitening compositions would be a welcome addition to the art.

BRIEF SUMMARY

An embodiment of the present disclosure is directed to a tooth whitening oral care composition. The oral care composition is made by combining ingredients comprising flakes of a water soluble whitening film, a dye with a hue angle in the CIELAB system ranging from 200 to 320 degrees, and an orally acceptable carrier vehicle. The flakes of the water soluble whitening film comprise: (a) a film-forming polymer comprising hydroxyalkyl cellulose wherein the hydroxyalkyl cellulose has a viscosity of about 1 to about 1000 millipascal seconds (mPa·s) as determined as a 2% by weight aqueous solution of the film-forming polymer at 20° C. using a Ubbelohde tube viscometer; and (b) a pigment with a hue angle in the CIELAB system ranging from 200 to 320 degrees.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An embodiment of the present disclosure is directed to a tooth whitening oral care composition. The composition is made by combining ingredients comprising water soluble polymer flakes, at least one dye having a hue angle in the CIELAB system ranging from about 200 to about 320 degrees, and an orally acceptable carrier vehicle. The water soluble polymer flakes comprise: (a) a film-forming polymer comprising hydroxyalkyl cellulose wherein the hydroxyalkyl cellulose has a viscosity of about 1 to less than about 1000 millipascal seconds (mPa·s) as determined as a 2% by weight aqueous solution of the polymer at 20° C. using a Ubbelohde tube viscometer; and (b) at least one pigment having a hue angle in the CIELAB system ranging from about 200 to about 320 degrees.

Flakes Comprising Pigments

The flakes can be made in any desired manner. In an embodiment, the flakes can be made from a water soluble film, referred to sometimes herein as "film flakes." The flakes comprise a matrix material comprising the water soluble hydroxyalkyl cellulose polymer in which the pigment is dispersed. In preparing film flakes according to the present disclosure, the hydroxyalkyl cellulose and pigment are dissolved in a compatible solvent (e.g., water, ethyl acetate, acetone, an alcohol such as ethanol, or mixtures thereof) to form a film-forming composition. Optionally, other ingredients may be added, e.g., a flavorant, humectant (e.g., propylene glycol), surfactant (e.g., Tween 80), sweetener, active agent and the like. The optional ingredients can be present in the film, in the non-film portion of the oral composition or both, and more detailed descriptions of such optional ingredients are provided hereinafter. The film-forming composition is cast on a releasable carrier and dried to form a sheet of film matrix material. The carrier material must have a surface tension which allows the film solution to spread evenly across the intended carrier width without soaking to form a destructive bond between the film and the carrier substrate. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

Any suitable film thickness can be employed. Examples of suitable thicknesses range from about 1 mil to about 5 mil, or about 1 mil to about 4 mil, or about 1.5 mil to about 5 mil, or about 1.5 mil to about 3 mil, or about 2 mil to about 3 mil, or about 2 mil.

Once the film is formed, the film flakes are made from the film, for example by punching or cutting the film into various shaped flakes such as hearts, squares, rectangles, triangles, stars, diamonds, circles, and the like. Optionally, the film may be ground into irregular shapes using convention grinding techniques known in the art. In an embodiment, the particle sizes of the film flakes are such that greater than 90% of the particles pass through a 50 mesh filter. In some embodiments the particle size is between 30 to 100 mesh, or 30 to 80 mesh, or 50 to 80 mesh. The film flakes are incorporated in the oral composition of the present disclosure at a concentration of about 0.05 to 5.0% by weight relative to the total weight of the oral composition, such as about 0.05 to 2% by weight, in another embodiment about 0.05 to 1% by weight, and in another embodiment about 0.1 to about 0.5% by weight.

The film flakes of the disclosure have a rapid dissolution rate, e.g., about 30 seconds or less, in another embodiment about 1 to 30 seconds, in another embodiment about 1 to 25 seconds, in another embodiment about 1 to 20 seconds, in another embodiment about 2 to 15 seconds. For purposes of this disclosure, the dissolution rate is defined as the average amount of time it takes for the film flakes to disintegrate and release observable color during toothbrushing, as determined in an in vivo study comprising 8 or more subjects using toothpaste containing the film flakes.

The film-forming polymer comprises a hydroxyalkyl cellulose polymer. In one embodiment the film-forming polymer consists essentially of a hydroxyalkyl cellulose polymer, that is, no other film-forming polymers, such as starch or Gantrez® are present in the film.

The film-forming polymer used to prepare the film matrix of the present disclosure is a water soluble hydroxyalkyl cellulose such as hydroxypropylmethyl cellulose, hydroxyethylpropyl cellulose, and hydroxybutylmethyl cellulose. The alkyl can be, for example, a $C_{1-5}$ alkyl, such as a $C_{1-4}$ alkyl. The film-forming cellulose polymer is a low viscosity polymer. By low viscosity is meant a viscosity in the range of about 1 to less than about 1000 millipascal seconds (mPa·s) as determined for a 2% by weight aqueous solution of the polymer at 20° C. using a Ubbelohde tube viscometer. In a more particular embodiment the viscosity of the polymer is about 1 to about 100, more particularly about 1 to about 20, and in a particular embodiment about 1 to about 10 mPa·s at 20° C. In a preferred embodiment the hydroxyalkyl cellulose polymer is hydroxypropylmethyl cellulose polymer (HPMC).

HPMC is available commercially from the Dow Chemical Company under the trade designation Methocel E5 LV. Methocel E5 LV is a USP grade, low viscosity HPMC having 29.1% methoxyl groups and 9% hydroxypropyl group substitution. It is a white or off-white free-flowing dry powder. As a 2 wt. % solution in water as measured with an Ubbelohde tube viscometer, it has a viscosity of 5.1 mPa·s at 20° C.

The hydroxyalkyl cellulose is incorporated in the film in amounts ranging from about 10 to about 80% by weight and preferably about 30 to about 60% by weight of the film. The hydroxyalkyl cellulose polymer is incorporated into the oral composition at, for example, from about 0.01 to about 10% by weight, such as about 0.05 to about 5%, or about 0.1 to about 1% by weight of the composition.

As discussed in co-pending Application No. PCT/US2013/77373, the disclosure of which is incorporated herein by reference in its entirety, the HPMC polymer is capable of delivering blue pigment to teeth when incorporated into a dentifrice formula. However, the ability of HPMC to deliver blue pigment appears to be enhanced when the HPMC is premixed and concentrated with the blue pigment in the flakes of the present disclosure. The blue pigment and HPMC remain together in the film flakes until the time of brushing when the flakes dissolve.

In an embodiment, the film flakes comprise about 0.01 to about 5% or more, such as about 0.015 to about 5%, or about 0.015 to about 3% by weight of the oral composition of the disclosure.

The film matrix of the present disclosure dissolves in water or an aqueous solution, such as saliva, during use. During tooth brushing, the mechanical action aids in rupture of the film flakes, which makes the film flakes more readily soluble in the aqueous environment. In the context of this disclosure, a "soluble" hydroxyalkyl cellulose is a material that is soluble in water. For example, the hydroxyalkyl cellulose can have a solubility of 0.5% or greater, such as 5% or greater by weight, at 25° C. Further, such a material remains soluble following drying from a solution state—i.e., it can be redissolved following drying. Such materials are film-forming polymers. Water solubility is required in order to avoid build up of the polymer on the teeth.

The hydroxyalkyl cellulose polymer is a deposition aid. That is, it is capable of enhancing the depositing or placing of the pigment onto the teeth and thereby enhances the color change caused by the pigment.

Any suitable amount of pigment can be employed. The amount of pigment in the oral composition can be, for example, from about 0.01 to about 0.3%, more particularly from about 0.02 to about 0.1%, and more particularly from about 0.03 to about 0.08% by weight. The pigment may be uniformly spread throughout the composition, or it may be dispersed in a second phase (e.g., a separate portion) such as a stripe or other coextruded second phase. Such "dual phase" compositions have the advantage that the phases may be differently colored, presenting a more visually attractive product to the consumer.

In an embodiment, the pigment has a blue-green to violet-red color, such as blue-green to blue-violet, or blue. Known pigments suitable for use in the formulations of the present disclosure are listed in the Colour Index International. Examples of such pigments are listed as pigment violet 1 through pigment violet 56 and pigment blue 1 through 83. Examples of pigment violets are pigment violet 1, 1:1, 1:2, 2, 3, 5:1, 13, 19, 23, 25, 27, 31, 32, 37, 39, 42, 44 and 50. Examples of pigment blues are pigment blue 1, 2, 9, 10, 14, 15, 15:1, 15:2, 15:3, 15:4, 15:6, 16, 18, 19, 24:1, 25, 56, 60, 61, 62 and 66. Other suitable pigments are pigment ultramarine blue and ultramarine violet. The pigment can have a hue angle, h, in the CIELAB system of from about 200 to about 320 degrees, such as about 250 degrees and about 290 degrees. A detailed description of hue angle may be found on p. 57 of Colour Chemistry 3rd edition by H. Zollinger published by Wiley-VCH.

While the preferred single pigments are blue or violet, the same effect may be achieved through mixing pigments outside of this h range; for example, such a hue angle may also be obtained by mixing a red and blue pigment to yield a blue or blue-violet shaded pigment. In an embodiment, the pigment is Pigment Blue 15, such as one or more of Pigment Blue 15:1, 15:2, 15:3, 15:4, 15:5 or 15:6. The hue angles and color for the pigment blue 15:1-15:6 series are defined as set forth at "The Porphyrin Handbook," vol. 19, Applications of Phthalocyanines, pp. 133-134, the disclosure of which is hereby incorporated by reference in its entirety. The pigment can be capable of reflecting sufficient light such that the treated tooth is perceivably whiter than its initial color. Preferably, the pigment is colored such that its natural color is within the violet-red to green-blue color, such as from violet to blue.

In an embodiment, a red pigment is used in addition to the green-blue to violet-red color pigment. If a red pigment is used, the red pigment can be present in a weight ratio of red pigment:green-blue to violet-red color pigment of about 0.1:1 to about 1:1, such as for example a ratio of red pigment:blue pigment of about 0.1:1 to about 1:1. Examples of red pigment include Red 30, Red 40, and the like.

A pigment is generally understood to be a material that changes the color of reflected light and that is insoluble in the relevant medium, at the relevant temperature. This is in contrast to dyes which are soluble. In the context of this disclosure, the "relevant medium" is human saliva (perhaps mixed with water), which is the liquid medium in which the composition is used, and the "relevant temperature" is the temperature of the oral cavity during brushing of the teeth, such as up to about 37° C. As a reasonable approximation, the relevant medium may be considered to be water and the relevant temperature to be 25° C.

The hydroxyalkyl cellulose in the film flakes aids the deposition of the pigment onto the teeth such that tooth surface whiteness is enhanced by at least 20% and more preferably by at least 100%, in comparison to the value obtained for teeth treated in an equivalent manner with a control formulation using the same amount of pigment in the absence of the hydroxyalkyl cellulose. A method for determining tooth whiteness is described in the Examples.

Delta b* is a magnitude of color change along a yellow-blue axis, negative delta b* corresponding to reduced yellowness.

Dye

Employing a dye with the pigment compositions of the present disclosure to achieve improved whitening is not a straight-forward endeavor. This is at least because dyes have significantly different properties than pigments. In particular, dyes are much more soluble in water than pigments. The solubility of dyes makes them more difficult to deposit and to be retained on teeth, especially in relatively high water content formulations of about 20 to about 30% by weight water or more. For example, EP1935395, the disclosure of which is incorporated herein by reference in its entirety, discusses the potential ineffectiveness of dyes as a whitener in cases where the dyes wash off the teeth. Polymers such as PVM/MA have been used to aid in depositing the blue dye on the teeth.

The pigment formulations of the present disclosure, on the other hand, employ water soluble polymer flakes. The flakes dissolve with brushing and have been found to aid in depositing the pigment on the surface of teeth. The relatively high amounts of water in the formulations allow the flakes to dissolve quickly during application to the teeth, such as during brushing. This is because the amount of water in the formulations, while being insufficient to substantially dissolve the flakes, is near the dissolution point, so that when water and/or saliva is introduced during brushing the flakes dissolve quickly. The high amount of water used in these formulations was generally thought to be incompatible with use of dyes, especially in the absence of a polymer adhesive aid, such as PVM/MA. However, Applicants have unexpected found that the combination of a dye with the pigments of the present disclosure can enhance the whitening effect above that of either the pigment or dye alone.

The dye employed in the compositions of the present disclosure can be any dye that will provide the desired whitening effect. In an embodiment, the dye has a hue angle, h, in the CIELAB system of from about 200 to about 320 degrees, such as from about 250 to about 290 degrees. A detailed description of hue angle may be found on p. 57 of Color Chemistry (Synthesis, Properties, and Applications of Organic Dyes and Pigments), 3rd edition by H. Zollinger published by Wiley-VCH (2001). In an embodiment, the dye has a blue to blue-violet color. While the preferred single dyes are blue or violet, the same effect may be achieved through mixing dyes outside of this h range; for example, such a hue angle may also be obtained by mixing a red and blue dye to yield a blue or blue-violet shaded dye. The dye can be capable of reflecting sufficient light such that the treated tooth is perceived by the human eye to be whiter than its initial color. For example, the dyes used to achieve this effect can be colored such that its natural color is within the violet-red to green-blue color range, such as from violet to blue.

As described above, the dyes are water soluble. The term "water-soluble" in this particular context generally means that the dye has an aqueous solubility of at least 10 g/L at 25° C., most preferably at least 100 g/L at 25° C. (where the solubility is determined in un-buffered distilled water). Triarylmethane dyes are examples of water soluble dyes useful in the compositions of the present disclosure. In some embodiments, dyes useful herein are anionic triphenylmethane dyes, and especially diaminotriphenylmethane dyes containing from two to four sulphonate groups, such as those corresponding to general formula (I):

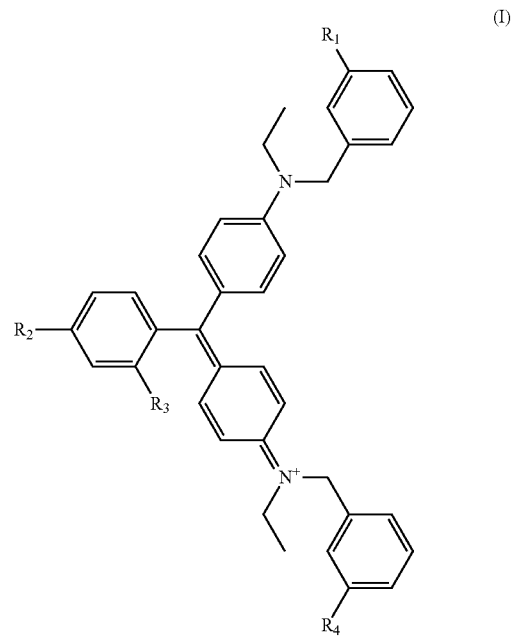

in which $R_1$, $R_2$, $R_3$ and $R_4$ are monovalent moieties that are each independently selected from hydrogen (—H), hydroxyl (—OH), halo (e.g. —Cl) and sulphonate (—$SO_3^-$) groups, with the proviso that at least two of $R_1$ to $R_4$ are sulphonate groups.

An example of a dye useful herein is FD&C Blue #1, also known as Brilliant Blue FCF (Blue 1) as well as other commercial names, which corresponds to general formula (I), wherein $R_2$ is —H and $R_1$, $R_3$, and $R_4$ are sulphonate groups. FD&C Blue #1 (CAS No. [3844-45-9]) is a colorant that induces a color change for foods and other substances. It is denoted by E number E133 and has a color index of 42090 (CI 42090). It has the appearance of a reddish-blue powder. It is soluble in water, and the solution has a maximum absorption at a wavelength of about 628 nanometer. It is a synthetic dye produced using aromatic hydrocarbons from petroleum. It is usually a disodium salt. The diammonium salt (D&C Blue #4) has CAS No. [2650-18-2]. Calcium and potassium salts are also known. Other dyes useful herein are FD&C Blue #2 (Indigo Carmine, CI 73015, CAS No. [860-22-0]), CI Food Blue 5 (CI 42051; also known as Acid Blue 3. CAS No. [3536-49-0]), Acid Blue 1 (CI 42045, CAS No. [129-17-9]) and the like. In some embodiments, the dye is FD&C Blue#1, FD&C Blue #2, D&C Blue #4, CI Food Blue 5, Acid Blue 1, or a mixture thereof.

Mixtures of dyes also can be used even if an individual dye has a hue angle outside the desired range as long as the mixture of dyes will be within the range. For example, red dyes, e.g., FD&C Red #3, FD&C Red #40, and the like, can be used. In one embodiment FD&C Blue #1 is used in combination with FD&C Red#40.

Any suitable amount of dye can be employed in the oral care composition. Example amounts can be from about 0.001 to about 2 weight %, from about 0.002 to about 1.5 weight %, from about 0.003 to about 1.25 weight %, from about 0.004 to about 1 weight %, from about 0.005 to about 0.5 weight %, from about 0.0075 to about 0.25 weight %, from about 0.01 to about 0.1 weight %, from about 0.02 to about 0.07 weight %, or from about 0.03 to about 0.05 weight %. In some embodiments, the amount of dye in the oral care composition is about 0.03 weight %. In some embodiments, the amount of dye in the oral care composition is about 0.05 weight %. The dye may be uniformly spread throughout the composition or, it may be dispersed in a second phase or portion such as a stripe or other coextruded second phase. Such "dual phase" compositions have the advantage that the phases may be differently colored, presenting a more visually attractive product to the consumer.

Whiteness-Enhancing Adhesive Materials

It has been surprisingly discovered that a number of ingredients increase dye deposition, adherence, and concomitant tooth whiteness when present in compositions of the present disclosure. Such ingredients are referred to herein as "whiteness-enhancing bio-adhesive materials".

In compositions of the present disclosure, these whiteness-enhancing bio-adhesive materials can be phosphorylated acrylic polymers, or copolymers of a vinyl ether and maleic acid or maleic anhydride. In some embodiments, the copolymer of a vinyl ether and maleic acid or maleic anhydride is a copolymer of vinylmethylether and maleic acid ("PVM/MA"). Unlike prior art compositions that use a dye and an adhesive material, in the compositions of the present disclosure the dye is not covalently bonded to the whiteness-enhancing bio-adhesive material (see, e.g., US Patent Application Publication 2012/0093905). That said, it may be possible that the hydroxyalkyl cellulose functions as a bioadhesive for the dye in the compositions of the present disclosure. Thus, in an embodiment, the oral care composition does not include more than trace amounts of a bio-adhesive polymer, wherein the bio-adhesive polymer is different than the hydroxyalkyl cellulose.

The whiteness-enhancing bio-materials of the present disclosure may help deposit the dye onto the teeth such that tooth surface whiteness is enhanced by at least 20%, or by at least 100%, or by at least 400%, in comparison to the whiteness value obtained for teeth treated in an equivalent manner with a control formulation using the same amount of dye in the absence of the whiteness-enhancing material. A method for determining tooth whiteness is described in the Examples.

In some embodiments the amount of the copolymer of a vinyl ether and maleic acid or maleic anhydride in the compositions is from 0.001 to 10 weight %, from 0.01 to 6 weight %, from 0.01 to 5 weight %, from 0.05 to 5 weight %, from 0.1 to 5 weight %, from 0.5 to 5 weight %, from 1 to 4 weight %, from 1 to 2 weight % copolymer, or about 2 weight %. Other compositions of the present disclosure include 0.3 to 0.8 weight %/o copolymer and more particularly include 0.3 to 0.6 weight % copolymer.

In one embodiment the whiteness-enhancing material is a copolymer of vinylmethylether and maleic acid. In some embodiments such copolymers are 1:4 to 4:1 copolymers of maleic acid with methylvinyl ether having molecular weight (MW) of 30,000 Daltons to 1,000,000 Daltons, most preferably 30,000 Daltons to 500,000 Daltons. These copolymers are available for example as GANTREZ® series copolymers. Particularly preferred copolymers include GANTREZ® S-96 and GANTREZ® S-97, which are available in powder and solution forms. When the solution form is used, an appropriately calculated higher amount may be added so that the level of the active ingredient may be maintained.

In one embodiment the whiteness-enhancing material is a phosphorylated acrylic polymer. In some embodiments, the compositions include from 0.001 to 10 weight/o, from 0.01 to 6 weight %, from 0.01 to 5 weight %, from 0.05 to 5 weight %, from 0.1 to 5 weight %, from 0.5 to 5 weight %, from 1 to 4 weight %, from 1 to 2 weight % copolymer, or about 2 weight % of the phosphorylated acrylic polymer.

In an embodiment, only trace amounts, or none, of the whiteness enhancing bio-adhesive materials described herein above are included in the formulations of the present disclosure. For purposes of the present disclosure, the term "trace amounts" is defined to mean less than 0.0001% by weight relative to the total weight of the composition.

Orally Acceptable Carrier Vehicle

The oral care compositions of the present disclosure include a vehicle or base into which the film flakes are incorporated. Examples of orally acceptable carrier vehicles include carrier polymers, humectants, water, abrasives, thickeners such as silicas or any combination of two or more thereof. The term "orally-acceptable" refers to a polymer or ingredient which can be used or applied to the oral cavity in a safe manner during normal use.

Carrier Polymers

Carrier polymers can comprise one or more anionic or nonionic polymers, and also may include additional polymers to adjust the viscosity of the formulation or enhance the solubility of other ingredients.

Suitable carrier polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Anionic polymers useful herein may enhance the effect of the water insoluble whitening complex, for example in an amount of from about 0.001 to about 5%, more particularly about 0.01 to 5%, more particularly about 0.05 to 4%, more particularly about 0.05 to 3% of the composition. Examples of such agents are taught in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez®, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers can contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference in its entirety. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 to Sikes et al., incorporated herein by reference in its entirety.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Hydroxyalkyl methyl cellulose may also be present in the non-film portion of the oral composition. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to about 5%, more particularly about 0.5 to about 5% by weight of the total composition are used. Orally acceptable carrier polymers for use in the disclosure can be water soluble. Suitable orally acceptable carrier polymers for use in the disclosure will generally dissolve or disperse in water at a temperature of 25° C. In addition to the hydroxyalkyl methyl cellulose in the film flakes, certain orally acceptable carrier polymers also are able to help deposit the pigment onto the teeth such that tooth surface whiteness is enhanced.

The amount of orally acceptable carrier vehicle polymer in compositions of the disclosure, whether enhancers, deposition aids, thickeners or the like, or of a combination thereof, suitably ranges from about 0.001 to about 10%, more particularly about 0.005 to about 5%, more particularly about 1 to about 5%, and more particularly about 1 to about 3%.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Abrasives

The compositions can comprise a calcium phosphate abrasive, e.g., tricalcium phosphate ($Ca_3(PO_4)_2$), hydroxyapatite ($Ca_{10}(PO_4)(OH)_2$), or dicalcium phosphate dihydrate ($CaHPO_4.2H_2O$, also sometimes referred to herein as DiCal) or calcium pyrophosphate. Other abrasives that can be used in addition to or in place of calcium phosphate abrasives include, for example, silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasives polishing materials useful herein, as well as the other abrasives, generally have an average particle size ranging between about 0.1 and about 30 microns, or about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Examples of commercially available low oil absorption silica abrasives are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive. The abrasive is present in the oral care composition at a concentration of, for example, about 10 to about 60% by weight, in other embodiment about 20 to about 45% by weight, and in another embodiment about 30 to about 50% by weight.

Water

Water is also present in the oral compositions of the disclosure. Water, employed in the preparation of commercial oral compositions can be deionized and free of organic impurities. The amount of water can range from 18% or more, such as about 20% to about 35%, such as about 20% to about 30%, by weight of the oral compositions. This amount of water includes the free water which is added plus that amount which is introduced with other materials such as with sorbitol or any components of the disclosure. In one embodiment no added water is included.

Product Form

Examples of suitable product forms for compositions of the disclosure include dentifrices, chewing gums and lozenges.

A type of product form of the present disclosure is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. The dentifrice can be used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Active Agents

The effective concentration of the active ingredients for optional use herein will depend on the particular agent and the delivery system used. It is understood that a toothpaste may be diluted with water upon use, The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Active agents can include one or more of a fluoride ion source, an anti-calculus agent, an amino acid, a whitening agent, an antibacterial agent, and the like.

Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product.

Antibacterial agents may be included in the oral composition of the present disclosure and particularly noncationic halogenated diphenyl ethers agents which are desirable from considerations of effectiveness and safety such as 2',4,4' trichloro-2 hydroxy-diphenyl ether (Triclosan) and 2,2'-dihydroxy-5,5' dibromophenyl ether. The antibacterial agent, when present in the oral composition, is present in concentrations of about 0.05 to about 2% by weight and preferably 0.1 to about 1% by weight. Levels of antibacterial agents will vary. As an example, a triclosan toothpaste may contain about 0.3 wt % triclosan.

Agents used to diminish teeth sensitivity such as potassium chloride, potassium nitrate and potassium citrate may also be included in oral compositions of the present disclosure at concentrations of about 0.1 to about 10% by weight.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, and sodium monofluorophosphate as well as mixtures thereof. In certain embodiments, the oral care composition of the disclosure may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., or about 1450 ppm. The appropriate level of fluoride will depend on the particular application. A toothpaste for general consumer can have, for example, about 1000 to about 1500 ppm, with pediatric toothpaste having somewhat less. A dentifrice or coating for professional application can have, for example, as much as about 5,000 or even about 25,000 ppm fluoride. Fluoride ion sources may be added to the compositions of the disclosure at a level of about 0.01 wt. % to about 10 wt. % in one embodiment, or about 0.03 wt. % to about 5 wt. %, and in another embodiment, or about 0.1 wt. % to about 1 wt. % by weight of the composition in another embodiment. Weights of fluoride salts to provide the appropriate level of fluoride ion will obviously vary based on the weight of the counter ion in the salt.

Foaming Agents

The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present disclosure. Polyoxyethylene is also commonly known as polyethylene glycol ("PEG") or polyethylene oxide. The polyoxyethylenes suitable for this disclosure will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present disclosure. The amount of foaming agent in the oral care composition is about 0.01 to about 0.9% by weight, about 0.05 to about 0.5% by weight, and in another embodiment about 0.1 to about 0.2% by weight.

Anticalculus Agents

The oral composition can include at least one anticalculus composition, such as one or more of the anticalculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. Other useful anticalculus agents include polycarboxylate polymers and polyvinyl methyl ether/maleic anhydride (PVME/MA) copolymers, such as GANTREZ®.

Surfactants

The compositions useful in the disclosure may contain anionic and/or nonionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$, iv. higher alkyl aryl sulfonates such as sodium dodecyl benzene sulfonate (sodium lauryl benzene sulfonate), v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. In one embodiment, the anionic surfactant is present in a toothpaste at from about 0.3% to about 4.5% by weight, e.g., about 1.5%.

Nonionic surfactants include nonanionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing compounds that are reactive therewith and have long hydrophobic chains (e.g., aliphatic chains of about 12 to 20 carbon atoms), which condensation products ("ethoxamers") contain hydrophilic polyoxyehtylene moieties, such as condensation products of poly (ethylene oxide) with fatty acids, fatty alcohols, fatty amides and other fatty moieties, and with propylene oxide and polypropylene oxides (e.g., Pluronic® materials).

The compositions of the disclosure may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In an embodiment, the composition comprises sodium lauryl sulfate.

The surfactant or mixtures of compatible surfactants can be present in the compositions of the present disclosure in about 0.1% to about 5.0%, in another embodiment about 0.3% to about 3.0% and in another embodiment about 0.5% to about 2.0% by weight of the total composition.

Flavoring Agents

The oral care compositions of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The amount of flavoring agent in the individual oral care composition is about 0.001 to 0.05% by weight and in another embodiment about 0.005 to about 0.015% by weight.

Other Optional Ingredients

In addition to the above-described components, the embodiments of this disclosure can contain a variety of optional dentifrice ingredients some of which are described below. Optional ingredients include, for example, but are not limited to, sudsing agents, sweetening agents, and additional coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

In an embodiment, the flakes have less than 1% by weight starch, such as 0.1% or less, or 0.01% or less, relative to the total weight of the flakes. The term "free of starch" is defined herein to mean that no starch is added to the film-forming ingredients and the resulting film contains no measurable amount of starch.

The disclosure also includes a method for temporarily whitening teeth comprising administering an effective amount of the composition of the disclosure to the oral cavity of a subject in need thereof. The whitening effect of the composition is considered temporary in that its whitening effect will noticeably diminish with time, such as, for example, in about two weeks after application if not additionally treated.

Embodiments consistent with the present disclosure are further illustrated through the following non-limiting example(s).

EXAMPLES

Example 1—Preparation of Flakes Comprising Pigment

The list of ingredients shown in Table 1 were mixed together to form a liquid film-forming composition. From the film-forming composition, pigment containing films were cast comprising blue pigment 15. The only film-forming material in the formula was HPMC polymer, specifically sold under the trade name Methocel ES from Dow Corning. Methocel ES is a low molecular weight HPMC having a viscosity of 4-6 mPa·s for a 2% solution at 20° C. and a shear rate of 10 $s^{-1}$.

TABLE 1

| Ingredient | Wt. % |
|---|---|
| HPMC E5 | 55.2 |
| Blue Pigment 15 | 16.9 |
| Red 30 | 3.4 |
| Propylene Glycol | 20.7 |
| Tween 80 | 3.8 |

After casting, the resulting films were ground into small flakes comprising pigment.

Example 2—Dentifrice Formula Preparation

The small flakes of Example 1 were incorporated into a dentifrice formula made from the ingredients listed in Table 2.

TABLE 2

Formula composition

| Ingredient | Target Wt. % | Wt. % Range |
|---|---|---|
| Sorbitol | 29.4 | 5-35 |
| High Cleaning Silica | 22 | 10-25 |
| Water | 20 | 20-30 |
| Glycerin | 10 | 5-35 |
| Thickening Silica | 4.0 | 0-6 |
| Polyethylene Glycol | 3.0 | 0-10 |
| Sodium Lauryl Sulfate | 1.5 | 1-3 |
| Cocamidopropyl Betaine | 1.25 | 1-2 |
| Flavor | 1.2 | 1-3 |
| Sodium Carboxymethylcellulose | 0.5 | 0-1 |
| Sodium Fluoride | 0.32 | 0.22-0.32 |
| Sodium Saccharin | 0.30 | 0.1-0.5 |
| Blue Pigment 15 in HPMC film | 0.3 | 0.1-0.5 |
| Titanium dioxide coated mica | 0.25 | 0-1 |
| Xanthan Gum | 0.2 | 0-1 |
| FD&C Blue #1 | Varied as shown in Table 3 | 0.02-2.0 |

Three separate samples of the Blue Pigment HMPC film (0.05% blue pigment) containing the dentifrice base composition of Table 2 were prepared. Sample 1 included no added FD&C Blue #1 and was used as a control sample. FD&C Blue #1 was added to Samples 2 and 3 in the amounts of 0.05% and 0.10% respectively.

Example 3—Whitening Tests

The roots of human third molars were removed and each tooth was bisected from the crown through the root. Each half of the tooth was mounted in methacrylate resin and then secured in a brushing tray, enamel side facing out, using a thermal impression compound. Four teeth were mounted per tray. The teeth were brushed for 10 minutes with a 1:2 (w/w) silica toothpaste slurry to remove any extrinsic surface stains, rinsed with deionized water and dried with cool air. Baseline CieLab measurements were recorded with a spectrophotometer (Spectroshade Micro, MHT technologies).

The teeth as prepared above were then submerged in saliva (9 mL/tray) and aged at 37° C. with gentle agitation for 15 minutes. Test toothpaste (6 g) from each of Samples 1 to 3 above was then added to separate trays already containing 9 ml saliva. The teeth were brushed for 2 minutes using each sample toothpaste, rinsed with 100 mL deionized water, dried with cool air, and CieLab measurements were recorded.

After brushing, the teeth were again aged in saliva. CieLab measurements were recorded after 10 minutes and 30 minutes of aging in saliva. Teeth were rinsed and dried with cool air before CieLab measurements were recorded at each time point during the soaking cycle. Delta b* was reported and is the change in the yellow-blue axis in CieLab color space. This is the metric by which the deposition of bluing agent was quantified. The Delta b* reported in Table 3 below is the difference between the b* values of the tooth after surface stains were removed and the b* values after brushing with the product from each of Samples 1, 2 and 3 above. A change in whiteness index (WIO) is also reported to show that the deposition of bluing agent results in an increase in the whiteness of a tooth.

TABLE 3

| Samples Wt. % FD&C Blue#1 added to Samples | ΔWIO | | | Δb* | | |
|---|---|---|---|---|---|---|
| | Initial | 10 min saliva | 30 min saliva | Initial | 10 min saliva | 30 min saliva |
| Sample 1 - 0.00% | 4.6 | 4.1 | 2.9 | −1.3 | −0.7 | −0.4 |
| Sample 2 - 0.05% | 6.2 | 5.9 | 4.1 | −1.5 | −1.0 | −0.5 |
| Sample 3 - 0.10% | 7.6 | 5.8 | 3.4 | −2.0 | −1.2 | −0.6 |

The addition of FD&C Blue #1 to an oral care composition with 0.05% Blue Pigment 15 delivered from a HMPC film increased the overall whitening efficacy of the preparation as seen from the data in Table 3. This boost in whitening is surprising because blue dye alone has not been generally known to adhere to teeth well in a formulation with a relatively high water content, such as containing about 20% or more water as did the formulation above, without the use of a polymer such as PVM/MA.

Thus, the above examples demonstrate that oral care compositions containing FD&C Blue #1 dye and Pigment 15 in an HPMC polymer film, wherein the composition does not contain PVM/MA Copolymer, provides superior deposition of blue color compounds to the surface of a tooth compared to the same oral composition containing blue pigment alone, and thus improves whitening.

What is claimed is:

1. A tooth whitening oral care composition made by combining ingredients comprising:
   (i) flakes of a water soluble whitening film comprising
      (a) a film-forming polymer comprising hydroxyalkyl cellulose wherein the hydroxyalkyl cellulose has a viscosity of about 1 to about 1000 millipascal seconds (mPa·s) as determined as a 2% by weight aqueous solution of the film-forming polymer at 20° C. using a Ubbelohde tube viscometer; and (b) at least one pigment with a hue angle in the CIELAB system ranging from 200 to 320 degrees, wherein the flakes are made from said film by punching, cutting, or grinding the film such that greater than 90% of the particles pass through a 50 mesh filter or in order that the particle size is between 30 to 100 mesh;

(ii) at least one dye with a hue angle in the CIELAB system ranging from 200 to 320 degrees, and (iii) an orally acceptable carrier vehicle comprising water in an amount from 18% to about 35%, by weight, relative to the total weight of the composition;

wherein the oral care composition is a toothpaste or tooth gel.

2. The oral care composition of claim 1, wherein the hydroxyalkyl cellulose is hydroxypropyl methyl cellulose.

3. The oral care composition of claim 1, wherein the pigment comprises at least one blue or violet pigment chosen from Pigment Blue #1, Pigment Blue #2, Pigment Blue #9, Pigment Blue #10, Pigment Blue #14, Pigment Blue #15, Pigment Blue #15:1, Pigment Blue #15:2, Pigment Blue #15:3, Pigment Blue #15:4, Pigment Blue #15:5, Pigment Blue #15:6, Pigment Blue #16, Pigment Blue #18, Pigment Blue #19, Pigment Blue #24:1, Pigment Blue #25, Pigment Blue #56, Pigment Blue #60, Pigment Blue #61, Pigment Blue #62, Pigment Blue #66, pigment violet #1, pigment violet #1:1, pigment violet #1:2, pigment violet #2, pigment violet #3, pigment violet #5:1, pigment violet #13, pigment violet #19, pigment violet #23, pigment violet #25, pigment violet #27, pigment violet #31, pigment violet #32, pigment violet #37, pigment violet #39, pigment violet #42, pigment violet #44 and pigment violet #50.

4. The oral care composition of claim 1, wherein the dye is FD&C Blue #1, D&C Blue #4, calcium salts of FD&C Blue #1, potassium salts of FD&C Blue #1, FD&C Blue #2, CI Food Blue 5, Acid Blue 3, Acid Blue 1, or a mixture thereof.

5. The oral care composition of claim 1, wherein the dye is a mixture of a red dye and a blue dye.

6. The oral care composition of claim 1, wherein the oral care composition does not include more than trace amounts of a bio-adhesive polymer, wherein the bio-adhesive polymer is different than the hydroxyalkyl cellulose.

7. The oral care composition of claim 1, wherein the oral care composition does not include more than trace amounts of a methyl vinyl ether/maleic anhydride copolymer.

8. The oral care composition of claim 1, wherein the orally acceptable carrier vehicle comprises a humectant.

9. The oral care composition of claim 1, wherein the oral composition further comprises at least one active chosen from an anticaries agent and an anticalculus agent.

10. The oral care composition of claim 1, wherein the flakes are in an amount of about 0.01 to about 5% by weight of the oral care composition.

11. The oral care composition of claim 1, wherein the flakes are free of starch.

12. The oral care composition of claim 1, wherein the flakes further comprise at least one of a humectant or a surfactant.

13. The oral care composition of claim 1, wherein the orally acceptable carrier vehicle comprises at least one ingredient chosen from a carrier polymer, a humectant, water, an abrasive and a thickener.

14. The oral care composition of claim 1, further comprising an effective amount of an additional agent selected from fluoride, arginine in free or orally acceptable salt form, an antibacterial agent in addition to a gallium salt and a basic amino acid polymer, an anti-inflammatory agent, a whitening agent, and a combination of two or more thereof.

15. The oral care composition of claim 1, wherein oral care composition is a dentifrice.

16. The oral care composition of claim 1, wherein the oral care composition is a toothpaste comprising one or more of water, an abrasive, a surfactant, a foaming agent, a vitamin, a polymer, an enzyme, a humectant, a thickener, an antimicrobial agent, a preservative, a flavoring, a coloring and/or a combination of two or more thereof.

17. A method for temporarily whitening teeth comprising administering an effective amount of the oral care composition of claim 1 to the oral cavity of a subject.

* * * * *